United States Patent [19]

Schlingmann et al.

[11] Patent Number: 5,068,186

[45] Date of Patent: Nov. 26, 1991

[54] PROCESS FOR THE ENZYMATIC PREPARATION OF DISACCHARIDE FLUORIDES USING ALPHA-GLYCOSYL FLUORIDES AS SUBSTRATES

[75] Inventors: Merten Schlingmann, Königstein; Reinhold Keller, Bad Soden am Taunus; Matthias Wiesner, Mainz; Wolfgang Treder; Joachim Thiem, both of Münster, all of Fed. Rep. of Germany

[73] Assignee: Hoechst Aktiengesellschaft, Frankfurt am Main, Fed. Rep. of Germany

[21] Appl. No.: 545,143

[22] Filed: Jun. 14, 1990

Related U.S. Application Data

[63] Continuation of Ser. No. 216,276, Jul. 8, 1988, abandoned.

[30] Foreign Application Priority Data

Jul. 10, 1987 [DE] Fed. Rep. of Germany ....... 3722812

[51] Int. Cl.$^5$ .................. C12P 19/12; C12P 19/14; C12P 19/18; C12P 19/20
[52] U.S. Cl. .................................. 435/96; 435/97; 435/98; 435/99; 435/100; 435/193; 435/200; 435/208
[58] Field of Search .................. 435/96, 97, 98, 99, 435/100, 193, 200, 208

[56] References Cited

U.S. PATENT DOCUMENTS 4,859,590 8/1989 Thiem et al. .................. 435/97

FOREIGN PATENT DOCUMENTS 226563 6/1987 European Pat. Off. .

OTHER PUBLICATIONS

Okeda et al., "Carbohydrate Res.", vol. 71 (1979) pp. 287–298.
Derwent Abs. 87-171805/25 (EP-226563) Jun. 24, 1987 Nilsson.
Derwent Abs. 86-288890/44 (J61212297) Sep. 20, 1986 Tokuyama Soda.
Nicolaou et al., J. Am. Chem. Soc., 1984, 106, pp. 4189–4192 (See Scheme III, p. 4191, col. 1).
Chem. Abs. 109 (1988) 228758h Thiem et DE 3,626,213 Feb. 4, 1988.
Wong et al., J. Org. Chem., vol. 47, (1982) pp. 5416–5418.
Thiem et al., Angew. Chemie, vol. 98, (1986) pp. 1100–1101.
Hedbys et al., Biochem. and Biophys. Res. Com. vol. 123, No. 1 (1984), pp. 8–15.
Barnett et al., Biochem. J., vol. 103 (1967) pp. 699–704.
Barnett et al., Biochem. J., vol. 105 (1967) pp. 669–672.
Barnett et al., Biochem. J., vol. 123 (1971) pp. 607–611.
Gold et al., Biochem. and Biophys. Res. Com., vol. 42, No. 3 (1971), pp. 469–474.
Okada et al., Carbohydr. Res., vol. 26, (1973), pp. 240–243.
Kitahata et al., J. Biol. Chem., vol. 256, No. 12, (1981), pp. 6017–6026.

*Primary Examiner*—Herbert J. Lilling
*Attorney, Agent, or Firm*—Finnegan, Henderson, Farabow, Garrett and Dunner

[57] ABSTRACT

Disaccharide fluorides can be prepared by incubation of α-D-glycosyl fluorides in concentrated solutions with α-glycosidases.

5 Claims, No Drawings

PROCESS FOR THE ENZYMATIC PREPARATION OF DISACCHARIDE FLUORIDES USING ALPHA-GLYCOSYL FLUORIDES AS SUBSTRATES

This application is a continuation of application Ser. No. 07/216,276, filed July 8, 1988.

Enzymatic methods of glycosylation have attracted increasing attention recently because it is possible in this way to synthesize oligosaccharides specifically and with avoidance of long synthetic routes and elaborate protective group techniques [G. M. WHITESIDES, C.-H. WONG Angew. Chem. 97, 617 (1985)]. In this connection it is often possible, because the biological effect of the enzymes is known, to predict the mode and site of linkage of the resulting products. Particularly important for this are now the glycosyltransferases [C.-H. WONG, S. HAYNIE, G. M. WHITESIDES J. Org. Chem. 47, 5416 (1982); J. THIEM, W. TREDER Angew. Chem. 98, 1100 (1986)] and the glycosylases which bring about transglycosylation [(L. HEDBYS, P. O. LARSSON, K. MOSBACH, S. SVENSSON Biochem. Biophys. Res. Commun. 123, 8 (1984)]. It has been known since the studies of Barnett [J. E. G. BARNETT, W. T. S. JARVIS, K. A. MUNDAY Biochem. J. 103, 699 (1967) and 105, 699 (1967); J. E. G. BARNETT Biochem. J. 123, 607 (1971)] that glycosyl fluorides are cleaved by the relevant specific glycosyl hydrolases to give hydrogen fluoride and the corresponding carbohydrates. In the interim, a number of enzymes which accept glycosyl fluorides as substrate have been found.

Thus, it is possible to obtain glucose 1-phosphate from α-D-glucosyl fluoride with sucrose phosphorylase in the presence of phosphate [A. M. GOLD, M. P. OSBER Biochem. Biophys. Res. Commun. 42, 469 (1971)], to prepare a glycogen-like polysaccharide from α-D-glucoysl fluoride and fructose with amylosucrase [G. OKADA, E. J. HEHRE Carbohydr. Res. 26, 240 (1973)], or to synthesise α- and β-cyclodextrin, together with malto oligomers, with cyclodextrin-α(1->4)-glycosyltransferase (German Patent Application No. P 36 26 213.7). Disaccharide fluorides can also be used as substrates, as shown by the formation of malto oligomers from α-maltosyl fluoride [S. KITAHATA, C. F. BREWER, D. S. GENGHOF, T. SAWAI, E. J. HEHRE J. Biol. Chem. 256, 6017 (1981)].

It has now been found, surprisingly, that incubation of α-D-glycosyl fluoride with α-glycosidases in concentrated solution results not only in the cleavage to give the corresponding monosaccharide and hydrogen fluoride but also in the formation of oligomers and in the formation of disaccharide fluorides.

Thus the invention relates to a process for the preparation of disaccharide fluorides, which comprises transformation of α-D-glycosyl fluorides in concentrated solution using α-glycosidases.

The invention is explained in detail hereinafter and is defined in the claims.

Incubation with α-glycosidases in concentrated solutions of the appropriate α-glycosyl fluorides results, in a surprising manner, in oligomers which may also contain anomerically bonded fluorine. The concentrations of the glycosyl fluorides in the reaction solution ought to be about 30% to 60%, preferably 40% to 50%, especially 45%, based on the weight of the solution.

The enzyme can be used both in the free form and in immobilized form. The immobilized form is preferred because the space/time yield is better. For this purpose, the enzyme is, in general, adsorbed onto or covalently bonded, with or without spacers, to a carrier. Suitable are organic carriers such as, for example polyacrylonitrile, or inorganic carriers such as, for example, silica gel. It is particularly preferred for the enzyme to be covalently bonded to the carrier via a spacer, especially glutaraldehyde.

The transformation of the α-glycosyl fluoride is carried out in aqueous solution or in aqueous/organic mixtures with the ratio of aqueous solution to organic solvent being in the range 2:1 to 1:2, preferably 1:1. Examples of suitable solvent mixtures are water/($C_1$–$C_4$)alkanols, water/acetonitrile or water/acetone. The reaction is generally carried out at temperatures of 20° to 60° C., especially at 30° to 40° C., and at a pH of 5 to 8, preferably at pH 6 to 7. It is important, because of the hydrogen fluoride which is being liberated, to monitor the pH during the reaction and to maintain it at pH 6 to 7, for example by addition of solid sodium bicarbonate or cation exchangers.

The reaction time depends on the temperature chosen for the reaction. If the preferred temperature range is used, then the reaction time is expected to be about 2 to 4 hours.

The preferred substrates used are α-D-glucosyl fluoride and α-D-galactosyl fluoride. The transformation of α-D-glucosyl fluoride using α-glucosidase according to the invention results not only in glucose and hydrogen fluoride but also in the oligomers isomaltose and panose plus the compound isomaltosyl fluoride, which has not been described hitherto, probably by transfer of a glucose residue to α-D-glucosyl fluoride with retention of the carbon-fluorine bond. Since it is an activated disaccharide, it is of particular interest for chemical and enzymatic reactions and it can be prepared only with difficulty by conventional means.

The analogous reaction of α-D-galactosyl fluoride using α-galactosidase provides the hitherto unknown galactobiosyl fluoride besides other oligomers.

The compound isomaltosyl fluoride has the formula I;

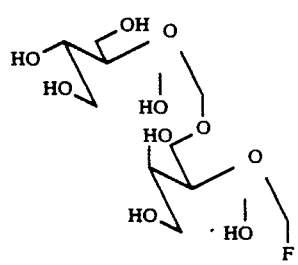

and the compound galactobiosyl fluoride has the formula II:

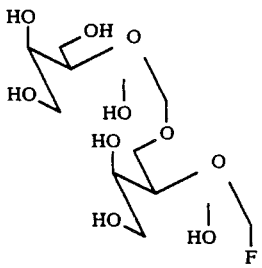

II

The invention is explained in full detail in the examples which follow. Unless otherwise indicated, percentage data relate to weight.

EXAMPLE 1

Transformation of α-D-glucopyranosyl fluoride

1. Immobilization of the Enzyme

α-glucosidase (α-D-glucoside glucohydrolase, E. C. 3.2.1.20) (57 U) is dissolved in 10 ml of a 0.05 M sodium acetate buffer (pH 6.5) and shaken with 5 g of a silica gel support functionalized with glutaraldehyde (Grace 332 250 A) at 20° C. for 4h [H. H. Weetall, Meth. Enzymol. 44, 134 (1976)]. The gel is then washed with 100 ml of double-distilled water, 200 ml of M NaCl and again with 200 ml of double-distilled water. The immobilized enzyme can now be used directly for the reaction. The gel can be stored at 4° C. without loss of activity for more than four weeks.

2. Synthesis of the Oligomers 1.5 g (8.2 mmol) of α-glucosyl fluoride are dissolved in 2 ml of 0.05 M sodium acetate buffer (ph 6.5), and immobilized α-glucosidase (42 U, 73% yield of immobilization) is added. The reaction solution is then incubated at 37° C. while shaking. The pH is maintained in the range between 6 and 7 by addition of solid NaHCO$_3$. The formation of product can be followed by TLC (propanol/ethanol/water, 5:3:2) by comparison with standards (α-D-glucosyl fluoride, glucose, maltose, maltotriose, maltotetraose, isomaltose). The reaction is stopped after 4 h, and the immobilized enzyme is removed by filtration, and the solution is freeze-dried.

Yield: 1.41 g of crude product.

The reaction mixture can be chromatographed on a RP18 HPLC column (0.8×50 mm, 7 μm, Merck) using water as eluent.

| Retention times: | |
|---|---|
| Isomaltose (6%) | 7.93 |
| Isomaltosyl fluoride (25%) | 7.12 |
| Panose (6%) | 12.18 |

Isomaltosyl fluoride: colorless syrup, $[\alpha]_D^{20} = +148.3°$ (c=0.84 in water)

$^1$H-NMR (D$_2$O):δ=5.70 (dd, H-1), 4.96 (d, H-1');J$_{1,2}$=3.2, J$_{1,F}$=52.5, J$_{1',2'}$=4.0 Hz.

The hitherto unknown isomaltosyl fluoride was also characterized as the heptaacetate after acetylation (acetic anhydride/pyridine, 12 h, 20° C.). 6-0-(2,3,4,6-tetra-O-acetyl-α-D-glucopyranosyl)-2,3,4-tri-O-acetyl-α-D-glucopyranosyl fluoride: colorless syrup, $[\alpha]_D^{20} = +91.2°$ (c=0.83 in methylene chloride)

$^1$H-NMR (CDCl$_3$):δ=5.72 (dd, H-1), 4.90 (ddd, H-2), 5.47 (dd, H-3), 5.12 (dd, H-4), 4.12 (m, H-5), 3.74 (dd, H-6a), 3.61 (dd, H-6b), 5.15 (d, H-1'), 4.82 (dd, H-2'), 5.47 (dd, H-3'), 5.04 (dd, H-4'), 4.01 (m, H-4'), 4.04 (dd, H-6a'), 4.25 (dd, H-6b'), 1.89, 1.92, 1.94, 1.97, 2.01, 2.03, 2.12 ppm (7s, 3H each, OAc); J$_{1,2}$=3.7, J$_{1,F}$=53.5, J$_{2,F}$=25.1, J$_{2,3}$=10.4, J$_{3,4}$=10.0, J$_{4,5}$=9.8, J$_{5,6a}$=4.0, J$_{5,6b}$=3.0, J$_{6a,6b}$=11.6, J$_{1',2'}$=3.5, J$_{2',3'}$=10.5, J$_{3',4'}$=9.0, J$_{4',5'}$=9.7, J$_{5',6a'}$=1.7, J$_{5',6b'}$=4.5, J$_{6a',6b'}$=12.0 Hz.

EXAMPLE 2

Transformation of α-D-galactopyranosyl fluoride

The α-galactosidase (α-D-glactoside galactohydrolase, E. C. 3.2.1.22) is immobilized as described in Example 1.

500 mg (2.75 mmol) of α-D-galactosyl fluoride are dissolved in 1 ml of 0.05 M sodium acetate buffer pH 6.5. Immobilized α-galactosidase (6.5 U on 1 ml of carrier, corresponding to example 1) is added. The solution is incubated at 37° C. with shaking. The pH of the reaction solution is maintained in the range between pH 6 and 7 by addition of cation exchanger (polystyrene-sulphonic acid resin, for example $^R$Dowex 50W×8). Formation of the product can be detected by thin-layer chromatography (propanol/ethanol/water, 5:3:2).

After 24 h, no new product formation is detectable, and the reaction is stopped by removing the immobilized enzyme by filtration. The product mixture is finally freeze-dried for further working up.

Galactobiosyl fluoride: colorless syrup :

$[\alpha]_D^{20} = +82.3°$ (c=0.74 in water)

$^1$H-NMR (D$_2$O):δ=5.68 (dd, H-1), 4.91 (d, H-1'); J$_{1,2}$=2.7, J$_{1,F}$=51.2, J$_{1',2'}$=3.8 Hz.

The crude product is acetylated (5 ml of pyridine, 3 ml of acetic anhydride, 12 h, 20° C.) and then chromatographed on a Sephadex LH-20 column (2.5×60 cm) with ethyl acetate as eluent.

Yield of 6-0-(2,3,4,6-tetra-O-acetyl-α-D-galactopyranosyl)-2,3,4-tri-O-acetyl-α-D-galactopyranosyl fluoride: 82 mg (9%) of syrup $[\alpha]_D^{20} = +101.4°$ (c=0.84 in chloroform)

$^1$H-NMR (CDCl$_3$):δ=5.72 (dd, H-1), 5.11 (ddd, H-2), 5.03 (dd, H-3), 5.26 (dd, H-4), 3.93 (ddd, H-5), 3.71 (dd, H-6a), 3.39 (dd, H-6b), 4.91 (d, H-1'), 5.03 (dd, H-2'), 5.27 (dd, H-3'), 5.26 (dd, H-4'), 4.09 (ddd, H-5'), 4.15 (dd, H-6a'), 4.31 (dd, H-6b'), 1.87, 1.88, 1.96, 2.02, 2.05, 2.09, 2.12 ppm (7s, 3H each, OAc); J$_{1,2}$=2.7, J$_{1,F}$=53.3, J$_{2,F}$=24.4, J$_{2,3}$=10.8, J$_{3,4}$=2.8, J$_{4,5}$=9.6, J$_{5,6a}$=7.6, J$_{5,6b}$=5.8, J$_{6a,6b}$=9.1, J$_{1',2'}$=3.5, J$_{2',3'}$=9.8, J$_{3',4'}$=2.8, J$_{4',5'}$=9.8, J$_{5',6a'}$=7.0, J$_{5',6b'}$=8.8, J$_{6a',6b'}$=9.0 Hz.

We claim:

1. A process for the preparation of disaccharide fluorides, which comprises incubation of reaction solutions containing 30% to 60% by weight of substrate of α-glycosyl fluorides in solution with αglycosidases selected from the group consisting of α-glucosidase and α-galactosidase in an amount sufficient to synthesize the disaccharide fluorides, the reaction being carried out at a pH of 6 to 7.

2. The process as claimed in claim 1, wherein reaction solutions containing 40% to 50% by weight of substrate are incubated.

3. The process as claimed in claim 1, wherein the reaction is carried out at 20° to 60° C.

4. The process as claimed in claim 3, wherein the reaction is carried out at 30° to 40° C.

5. The process as claimed in claim 1, wherein the substrate used is αD-glucosyl fluoride or α-D-galactosyl fluoride.

* * * * *